US008420853B2

(12) United States Patent  
Cho et al.

(10) Patent No.: US 8,420,853 B2
(45) Date of Patent: Apr. 16, 2013

(54) DERIVATIVES OF CYCLIC COMPOUND AND THE USE THEREOF

(75) Inventors: Hyunchul Cho, Pohang-si (KR); Yonghyun Choi, Seoul (KR); Jonghan Yhei, Seoul (KR)

(73) Assignees: Wonkisopharm Co., Ltd, Gwangju-Si (KR); Yonghyun Choi, Seoul (KR); Jonghan Yhei, Seoul (KR)

( * ) Notice: Subject to any disclaimer, the term of this patent is extended or adjusted under 35 U.S.C. 154(b) by 769 days.

(21) Appl. No.: 12/307,153

(22) PCT Filed: Jul. 2, 2007

(86) PCT No.: PCT/KR2007/003199
§ 371 (c)(1), (2), (4) Date: Aug. 4, 2009

(87) PCT Pub. No.: WO2008/004788
PCT Pub. Date: Jan. 10, 2008

(65) Prior Publication Data
US 2010/0022461 A1    Jan. 28, 2010

(30) Foreign Application Priority Data

Jul. 4, 2006 (KR) .................. 10-2006-0062703

(51) Int. Cl.
*C07C 43/20* (2006.01)
(52) U.S. Cl.
USPC ........... 560/220; 568/630; 568/648; 568/651; 560/130; 560/144; 560/221
(58) Field of Classification Search .................. None
See application file for complete search history.

(56) References Cited

U.S. PATENT DOCUMENTS 2,759,821 A * 8/1956 Jones et al. ................... 430/631
4,939,277 A * 7/1990 Imaki et al. ................... 549/476

FOREIGN PATENT DOCUMENTS

| EP | 1281744 A2 | 2/2003 |
| EP | 1717297 A1 | 11/2006 |
| JP | 2006-306773 A | 11/2006 |

OTHER PUBLICATIONS

Kawabata et al. Tetrahedron Letters, 2003, 44, 1545.*
Schauble et al Synthesis, 2005, 8, 1333-1339; STN abstract.*
Jarvis et al. J. Heterocyclic Chem. 1983, 20, 471-473.*
Arisawa et al J. Chem. Soc., Perkin Trans 1, 2002, 959-964.*
Walsh et al. The Journal of Bioligical Chemistry 1990, 265(8) 4374-4381.*
Jarvis, Bruce B., et al., "Bisallyl and bismethallyl derivative of 2,3-dihydroxypyridine," J. Heterocyclic Chemistry, 20(2), 1983, pp. 471-473.
Arisawa, Mitsuhiro et al., "Stereoselectivity in ring-closing olefin metathesis (RCM) of tethered dihexenoyl derivatives," J. Chemical Society, Perkin Transactions 1(7), 2002, 959-964.
Kawabata, Takeo et al., "Preparation and properties of chiral 4-pyrrolidinopyridine (PPY) analogs with dual functional side chains," Tetrahedron Letters, 44(8), 2003, 1545-48.
Schauble, J. Herman, et al., "Trans dialkoxylation of cyclic alkenes: A Prevost-type reaction," Synthesis, 8, 2005, 1333-39.
Park, Cheon Min, et al., "Palladium nanoparticles in polymers: catalyst for alkene hydrogenation, carbon-carbon cross-coupling reactions, and aerobic alcohol oxidation," Synthesis, 22, 2006, 3790-94.

* cited by examiner

*Primary Examiner* — Yevegeny Valenrod
(74) *Attorney, Agent, or Firm* — Sughrue Mion, PLLC

(57) ABSTRACT

Disclosed is tonovel cyclic derivatives having potent inhibiting effect on melanin formation and skin hyper-pigmentation activity with no adverse response to skin. They can be used as the therapeutics for treating and preventing the skin disease caused by over-reproduced melanin.

7 Claims, No Drawings

DERIVATIVES OF CYCLIC COMPOUND AND THE USE THEREOF

This is a National Stage application under 35 U.S.C. §371 of PCT/KR2007/003199 filed on Jul. 2, 2007, which claims priority from Korean patent application 10-2006-0062703 filed on Jul. 4, 2006, all of which are incorporated herein by reference.

TECHNICAL FIELD

The present invention relates to novel derivatives of cyclic compound showing potent skin-whitening activity, the composition containing the same and the use thereof.

BACKGROUND ART

Skin hyper-pigmentation comes of various origins such as the hormonal disorder followed by the inflammatory response of skin, genetic disease and ultraviolet irradiation, mainly the synthetic disorder and distribution disorder of melanin pigment, which results in skin discoloration, freckles, skin darkening after skin inflammation, purpura senile and so on.

The main function of melanin is to scavenge oxygen radical, which can protect skin from the injury. Therefore, it has been known that the plenty of melanin shows potent response on skin system for protecting skin from physical or chemical toxic substance. Melanin is formed by serial step i.e., converting tyrosine to dopaquinone by tyrosinase enzyme followed by further enzymatic reaction and spontaneous oxidative reaction and so on. Therefore, the inhibiting methods of melanin biosynthesis for protecting skin tanning are classified by follows: (1) LTV protecting method to get rid of the main cause of melanin formation, which is expected to give satisfactory results (2) Inhibiting method of core carbohydrate biosynthesis necessary to tyrosinase activity (3) Inhibiting method of the function of tyrosinase enzyme participating in melanin formation using kojic acid or arbutin (4) Inhibiting method of cell differentiation, using hydroquinone which has specific toxicity on melanocyte, melanin forming cell (5) De-colorizing method by reducing melanin formation.

In order to inhibit melanin biosynthesis, various skin-whitening materials such as hydroquinone, arbutin, ascorbic acid, kojic acid, and the extract of natural herb etc have been used till now. However, those conventionally available skin-whitening substances have several problems, for example; hydroquinone shows limit to use because of its sensitivity to skin, unfavorable staining or odor etc; ascorbic acid is easily oxidized under oxygen in the air, which results in unfavorable staining and odor of cosmetic preparation; herb extract is difficult to maintain its homogeneity and efficacy because of its various resources in spite of its strong skin whitening effect.

Besides the above-described skin-whitening materials, other skin-whitening substances have been developed recently as follows: for example, Korean Patent registration No. 509848 discloses skin-whitening cosmetic composition comprising khellactone derivatives isolated from *Peucedanum praeruptorum* as an active ingredient; and Korean Patent registration No. 479741 discloses skin-whitening cosmetic composition comprising glucose acylated derivatives as an active ingredient and so on. However those materials show several problems such as low-yield preparation etc.

Therefore, the present inventors have endeavored to find chemical compounds showing potent skin-whitening activity and finally found new cyclic derivatives showing various advantageous properties such as potent inhibiting effect on melanin formation and skin hyper-pigmentation activity with no adverse response to skin, or easiness to mass-production synthesis etc in the present invention.

DISCLOSURE OF INVENTION

Technical Problem

The present invention provides novel derivatives of cyclic compound and the pharmacologically acceptable salt thereof showing strong skin-whitening activity.

The present invention also provides a pharmaceutical composition comprising novel derivatives of cyclic compound and the pharmacologically acceptable salt thereof as an active ingredient in an effective amount to treat and prevent the skin disease caused by over-produced melanin.

The present invention also provides a cosmetic composition comprising novel derivatives of cyclic compound and the pharmacologically acceptable salt thereof as an active ingredient in an effective amount to treat and prevent the skin disease caused by over-produced melanin.

Technical Solution

Thus, the present invention provides novel derivatives of cyclic compounds, the pharmaceutically acceptable salt and the isomer thereof:

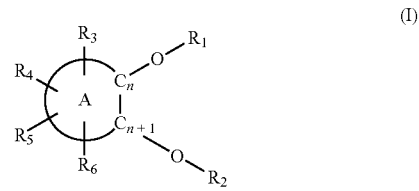

(I)

wherein

A ring is aliphatic or aromatic homo- or heterocyclic ring of which ring may includes at least one hetero atoms selected from an oxygen atom or a nitrogen atom, which may be fused with each other to form at least one fused ring;

$C_n$ and $C_{n+1}$ are adjacent carbon atoms in A ring of which n is positive integer;

$R_1$ and $R_2$ is saturated or unsaturated straight or branched alkyl group or acyl group;

$R_3$, $R_4$, $R_5$, and $R_6$ is independently at least one group selected from the group consisting of hydrogen atom, alkyl, alkoxy group, acyloxy group, acyloxymethyl group, oxo group, hydroxyl group, vinyl group, nitrile group, carboxyaldehyde group, carbonitrile group, and aldehyde group.

As preferable compounds of general formulae (I), the compounds of the present invention include following compounds wherein:

A ring is aliphatic ring selected from cyclohexane, cyclopentane, or benzene; or aromatic ring such as naphthalene; or heterocyclic ring fused with one or two 5-member ring or 6-member ring such as tetrahydrofuran, tetrahydropyran, pyridine, coumarin, decalin etc;

$R_1$ and $R_2$ is $C_3$-$C_{12}$ straight or branched saturated or unsaturated alkyl group, more preferably, $C_4$-$C_{10}$ straight or branched saturated or unsaturated alkyl group; or $C_3$-$C_{12}$ straight or branched saturated or unsaturated acyl group, more preferably, $C_4$-$C_{10}$ straight or branched saturated or unsaturated acyl group;

$R_3$, $R_4$, $R_5$, and $R_6$ is independently at least one group selected from the group consisting of hydrogen atom, $C_1$-$C_{10}$ alkyl, $C_1$-$C_{12}$ alkoxy group, acyloxy group, acyloxymethyl group, oxo group, hydroxyl group, vinyl group, nitrile group, carboxyaldehyde group, carbonitrile group, and aldehyde group.

The inventive compounds represented by general formula (I) can be transformed into their pharmaceutically acceptable salt and solvates by the conventional method well known in the art. For the salts, acid-addition salt thereof formed by a pharmaceutically acceptable free acid thereof is useful and can be prepared by the conventional method. For example, after dissolving the compound in the excess amount of acid solution, the salts are precipitated by the water-miscible organic solvent such as methanol, ethanol, acetone or acetonitrile to prepare acid addition salt thereof and further the mixture of equivalent amount of compound and diluted acid with water or alcohol such as glycol monomethylether, can be heated and subsequently dried by evaporation or filtrated under reduced pressure to obtain dried salt form thereof.

As a free acid of above-described method, organic acid or inorganic acid can be used. For example, organic acid such as methansulfonic acid, p-toluensulfonic acid, acetic acid, trifluoroacetic acid, citric acid, maleic acid, succinic acid, oxalic acid, benzoic acid, lactic acid, glycolic acid, gluconic acid, galacturonic acid, glutamic acid, glutaric acid, glucuronic acid, aspartic acid, ascorbic acid, carbonylic acid, vanillic acid, hydroiodic acid and the like, and inorganic acid such as hydrochloric acid, phosphoric acid, sulfuric acid, nitric acid, tartaric acid and the like can be used herein.

Further, the pharmaceutically acceptable metal salt form of inventive compounds may be prepared by using base. The alkali metal or alkali-earth metal salt thereof can be prepared by the conventional method, for example, after dissolving the compound in the excess amount of alkali metal hydroxide or alkali-earth metal hydroxide solution, the insoluble salts are filtered and remaining filtrate is subjected to evaporation and drying to obtain the metal salt thereof. As a metal salt of the present invention, sodium, potassium or calcium salt are pharmaceutically suitable and the corresponding silver salt can be prepared by reacting alkali metal salt or alkali-earth metal salt with suitable silver salt such as silver nitrate.

The pharmaceutically acceptable salt of the compound represented by general formula (I) comprise all the acidic or basic salt which may be present at the compounds, if it does not indicated specifically herein. For example, the pharmaceutically acceptable salt of the present invention comprise the salt of hydroxyl group such as the sodium, calcium and potassium salt thereof; the salt of amino group such as the hydrogen bromide salt, sulfuric acid salt, hydrogen sulfuric acid salt, phosphate salt, hydrogen phosphate salt, dihydrophosphate salt, acetate salt, succinate salt, citrate salt, tartarate salt, lactate salt, mandelate salt, methanesulfonate(mesylate) salt and p-toluenesulfonate (tosylate) salt etc., which can be prepared by the conventional method well known in the art.

There may exist in the form of optically different diastereomers since the compounds represented by general formula (I) have unsymmetrical centers, accordingly, the compounds of the present invention comprise all the optically active isomers, R or S stereoisomers and the mixtures thereof. Present invention also comprises all the uses of racemic mixture, more than one optically active isomer or the mixtures thereof as well as all the preparation or isolation method of the diastereomer well known in the art.

The compounds of the invention of formula (I) may be chemically synthesized by the methods which will be explained by following reaction schemes hereinafter, which are merely exemplary and in no way limit the invention. The reaction schemes show the steps for preparing the representative compounds of the present invention, and the other compounds also may be produced by following the steps with appropriate modifications of reagents and starting materials, which are envisaged by those skilled in the art.

General Synthetic Procedures

As depicted in following schemes, the compounds of the invention of formula (I) may be chemically synthesized by reacting diol (II) with acylating agents such as acyl halide or alkyl halide to perform esterification reaction or etherification of hydroxyl group in the cyclic ring; or further perform to hydrogenation thereto in the presence of organic solvent.

Scheme 1

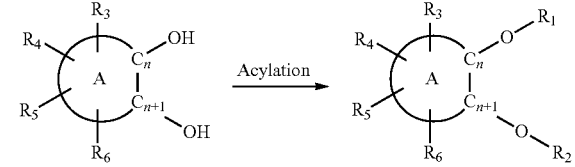

As depicted in above Scheme 1, the scheme explains the process for preparing compound (1) characterized in reacting diol (II) with acylating agents such as acyl halide or alkyl halide, for example, butyryl chloride, pentanoyl chloride, heptanoyl chloride, octanoyl chloride, 2-ethyl-hexanoyl chloride, lauroyl chloride, butanoic acid, 3-methyl-butyl bromide, pentyl bromide, to perform esterification reaction or etherification of hydroxyl group in the cyclic ring further perform to hydrogenation thereto in the presence of organic solvent such as dichloromethane, chloroform, THF, acetonitrile, DMF, pyridine etc.

Scheme 2

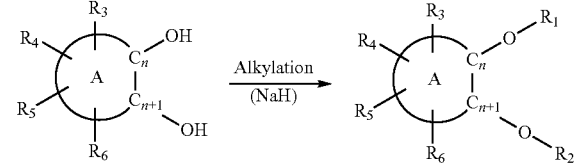

As depicted in above Scheme 2, the scheme explains the process for preparing compound (1) characterized in reacting diol (II) with alkylating agents, for example, metal hydride such as sodium hydride or metal carbonate such as potassium carbonate to hydrogenation thereto in the presence of organic solvent such as dichloromethane, chloroform, THF, acetonitrile, DMF, pyridine etc.

As depicted in Schemes 1 and 2, although the compounds of general formula (II) illustrate the cyclic ring having adjacent carbons having hydroxyl group, the present invention does not intend to limit thereto and the synthetic method of the present invention may be applied to the cyclic ring compounds which does not have adjacent two carbons with hydroxyl group or without hydroxyl group, such as cycloalkane, benzene, naphthalene, pyridine etc.

The most preferred compound of general formula (I) prepared by the method depicted in Scheme 1 in case that wherein A ring is cyclohexane; and $R_3$, $R_4$, $R_5$, and $R_6$ is a hydrogen atom, is one selected from the group consisting of:

1,2-dibutoxycyclohexane, 1,2-diisobutoxycyclohexane, 1,2-bis-pentyloxy-cyclohexane, 1,2-bis-(3-methyl-butoxy)-cyclohexane, 1-[2-(2-oxo-butoxy)-cyclohexyloxy]-butan-2-one, 1,2-bis(2,3-dimethyl-butoxy)-cyclohexane, 1,2-bis-(2,4-heptadienyloxy)-cyclohexane, 1,2-bis-(2,4-hexadienyloxy)-cyclohexane, 1,2-bis(2-ethyl-butoxy)-cyclohexane, 1,2-bis(2-ethyl-pentyloxy)-cyclohexane, 1,2-bis-(2-ethyl-hexyloxy)-cyclohexane, 1,2-bis-(2-heptenyloxy)-cyclohexane, 1,2-bis-(2-hexenyloxy)-cyclohexane, 1,2-bis-(2-methyl-butoxy)-cyclohexane, 1,2-bis-(2-methyl-pentyloxy)-cyclohexane, 1,2-bis-(2-methyl-2-pentenyloxy)-cyclohexane, 1,2-bis-(2-pentenyloxy)-cyclohexane, 1,2-bis-(3-heptenyloxy)-cyclohexane, 1,2-bis-(3-methyl-pentyloxy)-cyclohexane, 1,2-bis-(3-methyl-2-butenyloxy)-cyclohexane, 1,2-bis-(3-methyl-3-butenyloxy)-cyclohexane, 1,2-bis-(4-heptenyloxy)-cyclohexane, 1,2-bis-(4-hexenyloxy)-cyclohexane, 4-[2-(3-oxo-butoxy)-cyclohexyloxy]-butan-2-one, 3-methyl-4-[2-(2-methyl-3-oxo-butoxy)-cyclohexyloxy]-butan-2-one, 1,2-bis-(4-pentenyloxy)-cyclohexane, 1,2-bis-(5-heptenyloxy)-cyclohexane, 1,2-bis-(5-hexenyloxy)-cyclohexane, 5-[2-(4-oxo-pentyloxy)-cyclohexyloxy]-pentan-2-one, 1,2-bis-(5-methyl-hexyloxy)-cyclohexane, 1,2-bis-(6-heptenyloxy)-cyclohexane, 1,2-bis-hexyloxy-cyclohexane, 1,2-bis-heptyloxy-cyclohexane, 1,2-bis-octyloxy-cyclohexane, 1,2-bis-nonyloxy-cyclohexane, 1,2-bis-decyloxy-cyclohexane, 2-butenoic acid 2-(2-butenoyloxy)-cyclohexyl ester, 2-ethyl-butyric acid 2-(2-ethyl-butyryloxy)-cyclohexyl ester, 2-ethyl-hexanoic acid 2-(2-ethyl-hexanoyloxy)-cyclohexyl ester, hexanoic acid 2-hexanoyloxy-cyclohexyl ester, 2-methyl-2-butenoic acid 2-(2-methyl-2-butenoyloxy)-cyclohexyl ester, 2-methyl-2-pentenoic acid 2-(2-methyl-2-pentenoyloxy)-cyclohexyl ester, 2-methyl-3-butenoic acid 2-(2-methyl-3-butenoyloxy)-cyclohexyl ester, 2-methyl-4-pentenoic acid 2-(2-methyl-4-pentenoyloxy)-cyclohexyl ester, 2-methylbutanoic acid 2-(2-methylnutanoyloxy)-cyclohexyl ester, 2,2-dimethylpentanoic acid 2-(2,2-dimethylpentanoyloxy)-cyclohexyl ester, 2,4-hexadienoic acid 2-(2,4-hexadienoyloxy)-cyclohexyl ester, 2,4-pentadienoic acid 2-(2,4-pentadienoyloxy)-cyclohexyl ester, 2-methyl-heptanoic acid 2-(2-methyl-heptanoyloxy)-cyclohexyl ester, 2-methyl-hexanoic acid 2-(2-methyl-hexanoyloxy)-cyclohexyl ester, 2-methyl-pentanoic acid 2-(2-methyl-pentanoyloxy)-cyclohexyl ester, 2-pentenoic acid 2-(2-pentenoyloxy)-cyclohexyl ester, 3-methyl-2-butenoic acid 2-(3-methyl-2-butenoyloxy)-cyclohexyl ester, 3,3-dimethylbutanoic acid 2-(3,3-dimethylbutanoyloxy)-cyclohexyl ester, 3-hexenoic acid 2-(3-hexenoyloxy)-cyclohexyl ester, 3-methyl-2-butenoic acid 2-(3-methyl-2-butenoyloxy)-cyclohexyl ester, 3-methyl-4-pentenoic acid 2(3-methyl-4-pentenoyloxy)-cyclohexyl ester, 3-methylbutanoic acid 2-(3-methylbutanoyloxy)-cyclohexyl ester, 3-methyl-pentanoic acid 2-(3-pentanoyloxy)-cyclohexyl ester, 3-pentenoic acid 2(3-pentenoyloxy)-cyclohexyl ester, 4-methyl-2-pentenoic acid 2-94-methyl-2-pentenoyloxy)-cyclohexyl ester, 4-methyl-hexanoic acid 2-(4-methylhexanoyloxy)-cyclohexyl ester, 4-methyl-pentanoic acid 2-(4-methylpentanoyloxy)-cyclohexyl ester, 4-oxo-2-pentenoic acid 2-(4-oxo-2-pentenoyloxy)-cyclohexyl ester, 4-oxo-pentanoic acid 2-(4-oxopentanoyloxy)-cyclohexyl ester, 4-pentenoic acid 2-(4-pentenoyloxy)-cyclohexyl ester, 5-oxohexanoic acid 2-(5-oxohexanoyloxy)-cyclohexyl ester, 6-oxo-heptanoic acid 2-(6-oxoheptanoyloxy)-cyclohexyl ester, butanoic acid 2-butanoyloxy-cyclohexyl ester, pentanoic acid 2-pentanoyloxy-cyclohexyl ester, hexanoic acid 2-hexanoyloxy-cyclohexyl ester, heptanoic acid 2-heptanoyloxy-cyclohexyl ester, octanoic acid 2-octanoyloxy-cyclohexyl ester, 2-ethyl-hexanoic acid 2-(2-ethyl-hexanoyloxy)-cyclohexyl ester, decanoic acid 2-decanoyloxy-cyclohexyl ester, butyric acid 2-butyryloxy-trans-cyclohexyl ester, pentanoic acid 2-pentanoyloxy-trans-cyclohexyl ester, 3-methyl-2-butenoic acid 2-(3-methyl-2-butenoyloxy)-trans-cyclohexyl ester, hexanoic acid 2-hexanoyloxy-trans-cyclohexyl ester, heptanoic acid 2-heptanoyloxy-trans-cyclohexyl ester, octanoic acid 2-octanoyloxy-trans-cyclohexyl ester, 2-ethyl-hexanoic acid 2-(2-ethyl-hexanoyloxy)-trans-cyclohexyl ester, nonanoic acid 2-nonanoyloxy-trans-cyclohexyl ester, decanoic acid 2-decanoyloxy-trans-cyclohexyl ester, lauric acid 2-luroyloxy-trans-cyclohexyl ester, 3-methyl-2-butenoic acid 2-(3-methyl-2-butenoyloxy)-cis-cyclohexyl ester, 3-methyl-2-butenoic acid 2-(3-methyl-2-butenoyloxy)-trans-cyclopentyl ester, octanoic acid 2-octanoyloxy-trans-cyclopentyl ester, 2-ethyl-hexanoic acid 2-(2-ethyl-hexanoyloxy)-trans-cyclopentyl ester, 4-pentenoic acid 2-(4-pentenoyloxy)-trans-cyclohexyl ester, 3-methyl-2-butenoic acid 2-(3-methyl-2-butenoyloxy)-phenyl ester, octanoic acid 2-octanoyloxy-phenyl ester, 3-methyl-2-butenoic acid 3-(3-methyl-2-butenoyloxy)-naphthalene-2-yl ester, octanoic acid 3-octanoyloxy-naphthalene-2-yl ester, 2-ethyl-hexanoic acid 3-(2-ethyl-hexanoyloxy)-naphthalene-2-yl ester, octanoic acid 3-octanoyloxy-pyridine-2-yl ester, 3-methyl-2-butenoic acid 4-(3-methyl-2-butenoyloxy)-tetrahydrofuran-3-yl ester, 3-methyl-2-butenoic acid 2,3-bis-(3-methyl-2-butenoyloxy)-phenyl ester, octanoic acid 2,3-bis-octanoyloxy-cyclohexyl ester, myo-inositol hexa-O-butanoate, arabinopyranose 1,2,3,4-tetra-O-(3-methyl-2-butenoate), methyl-α-D-glucose tetra-O-butanoate, 1,2-bis-(3-methyl-butoxy)-cyclohexane, 1,2-bis-pentyloxy-cyclohexane, 1,2-bis-hexyloxy-cyclohexane and lauric acid 2-lauroyloxy-cyclohexyl ester, but does not limit thereto.

The most preferred compound of general formula (I) prepared by the method depicted in Scheme 1 in case that wherein A ring is cyclohexane; and $R_1$ and $R_2$ is 3-methyl-2-butenoyl group and $R_3$, $R_4$, $R_5$, and $R_6$ is a hydrogen atom, is one selected from the group consisting of:

3-methyl-2-butenoic acid 2-(3-methyl-2-butenoyloxy)-cyclohexyl ester, 3-methyl-2-butenoic acid 2-(3-methyl-2-butenoyloxy)-cyclopentyl ester, 3-methyl-2-butenoic acid 2-(3-methyl-2-butenoyloxy)-phenyl ester, 3-methyl-2-butenoic acid 2-(3-methyl-2-butenoyloxy)-naphthalene-1-yl ester, 3-methyl-2-butenoic acid 3-(30-methyl-2-butenoyloxy)-naphthalene-2-yl ester, 3-methyl-2-butenoic acid 2-(3-methyl-2-butenoyloxy)-naphthalene-3-yl ester, 3-methyl-2-butenoic acid 2-(3-methyl-2-butenoyloxy)-tetrahydropyran-3-yl ester, 3-methyl-2-butenoic acid 3-(3-methyl-2-butenoyloxy)-tetrahydropyran-4-yl ester, 3-methyl-2-butenoic acid 4-(3-methyl-2-butenoyloxy)-tetrahydrofuran-3-yl ester and 3-methyl-2-butenoic acid 3-(3-methyl-2-butenoyloxy)-tetrahydrofuran-2-yl ester, but does not limit thereto.

The novel derivatives of cyclic compounds prepared by the above-described method represented by general formulae (I) shows potent inhibiting effect on melanin production and skin hyper-pigmentation activity with no adverse response to skin, or easiness to mass-production synthesis etc in the present invention.

Accordingly, it is another object of the present invention to provide a pharmaceutical composition comprising an efficient amount of the compound represented by general formula (I) or the pharmaceutically acceptable salt thereof as an active ingredient in amount effective to treat and prevent the skin disease caused by over-reproduced melanin together with pharmaceutically acceptable carriers or diluents.

The term "the skin disease caused by over-reproduced melanin" disclosed herein includes skin discoloration, freckles, skin darkening after skin inflammation, purpura senile and so on.

In accordance with the other aspect of the present invention, there is also provided a use of the compound represented by general formula (I) or the pharmaceutically acceptable salt thereof for manufacture of medicines employed for treating and preventing the skin disease caused by over-reproduced melanin in mammals including human as an active ingredient in amount effective to inhibit over-production of melanin.

In accordance with the other aspect of the present invention, there is also provided a method of inhibiting over-production of melanin, wherein the method comprises administering a therapeutically effective amount of the compound represented by general formula (I) or the pharmaceutically acceptable salt thereof into the mammals including human suffering from said the disease caused by over-production of melanin.

The compound according to the present invention can be provided as a pharmaceutical composition containing pharmaceutically acceptable carriers, adjuvants or diluents. For example, the compound of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them. For topical administration, the compound of the present invention can be formulated in the form of ointments and creams.

It is confirmed that present compounds showed potent inhibiting activity of melanin production by following experiments for determining the inhibition of melanin production.

Hereinafter, the following formulation methods and excipients are merely exemplary and in no way limit the invention.

The compound of the present invention in pharmaceutical dosage forms may be used in the form of their pharmaceutically acceptable salts, and also may be used alone or in appropriate association, as well as in combination with other pharmaceutically active compounds.

The compound of the present invention may be formulated into preparations for injections by dissolving, suspending, or emulsifying them in aqueous solvents such as normal saline, 5% Dextrose, or non-aqueous solvent such as vegetable oil, synthetic aliphatic acid glycerides, esters of higher aliphatic acids, or propylene glycol. The formulation may include conventional additives such as solubilizers, isotonic agents, suspending agents, emulsifying agents, stabilizers, and preservatives.

The desirable dose of the inventive compound varies depending on the condition and the weight of the subject, severity, drug form, route and period of administration, and may be chosen by those skilled in the art. However, in order to obtain desirable effects, it is generally recommended to administer at the amount ranging 0.0001-100 mg/kg, preferably 0.001-10 mg/kg by weight/day of the inventive compound of the present invention. The dose may be administered in single or divided into several times per day. In terms of composition, the compound should be present between 0.0001 to 10% by weight, preferably, 0.0001 to 1% by weight based on the total weight of the composition.

The pharmaceutical composition of present invention can be administered to a subject animal such as mammals (rat, mouse, domestic animals or human) via various routes. All modes of administration are contemplated, for example, administration can be made by inhaled, orally, rectally or by intravenous, intramuscular, subcutaneous, intrathecal, epidural, intracerebroventricular injection, preferably, topical preparation for example, cream, gel, patch, spray, ointment, lotion, liniment, pasta, cataplasma etc., but not limited thereto.

It is the other object of the present invention to provide a cosmetic composition comprising cyclic compounds represent by general formula (I) and the pharmacologically acceptable salt thereof as an active ingredient in an effective amount to treat and prevent the skin disease caused by over-reproduced melanin It is preferable that the present cosmetic composition contains 0.001-40%, more preferably, 0.01-10% by the weight of the inventive composition based on the total weight of the composition. The other components may be a mixture of the ingredients of a conventional cosmetic composition well known in the art.

Cosmetic formulations containing above composition may be prepared in any form such as skin lotion, skin softner, skin toner, astringent, lotion, milk lotion, moisture lotion, nutrient lotion, massage cream, nutrient cream, moisture cream, hand cream, foundation, essence, nutrient essence, pack, cleansing foam, cleansing lotion, cleansing cream, body lotion, body cleanser, treatment, beauty solution and the like.

Hereinafter, the following formulation methods and excipients are merely exemplary and in no way limit the invention.

The cosmetic composition of the present invention can comprises additional additives selected from the group consisting of water soluble vitamin, lipid soluble vitamin, peptide polymer, polysaccharide polymer, sphingolipid and seaweed extract.

Preferable water soluble vitamins are any one which can be mixed with cosmetic, however, various vitamin such as vitamin $B_1$, $B_2$, $B_6$, pyridoxine, pyridoxine HCl, vitamin $B_{12}$, pantothenic acid, nicotinic acid, nicotinamide, folic acid, vitamin C, vitamin H etc., the salt thereof such as thiamin HCl salt, ascorbic acid Na salt etc or their derivatives such as ascorbic acid-2-phosphonic acid Na salt, ascorbic acid-2-phosphonic acid Mg salt are preferable and those can be obtained by conventional method such as microbial conversion method, purification method from the microbial cultivates, enzymatic method or chemical synthetic method.

Preferable lipid soluble vitamins are any one which can be mixed with cosmetic, however, various vitamin such as vitamin A, $D_2$, $D_3$, E (dl-a-tocopherol, d-a-tocopherol, d-d-tocopherol) and their derivatives such as palmitic acid ascorbate, stearic acid ascorbate, dipalmitic acid ascorbate, acetic acid-dl-a-tocopherol, nicotinic acid dl-a-tocopherol vitamin E, dl-pantothenyl alcohol, D-pantothenyl alcohol, pantothenyl ethylether etc. including the lipid soluble vitamin used in examples of present invention are preferable and those can be obtained by conventional method such as microbial conversion method, purification method from the microbial cultivates, enzymatic method or chemical synthetic method.

Preferable peptide polymers are any one which can be mixed with cosmetic, however, collagen, hydrolysable collagen, gelatin, elastin, hydrolysable gelatin, keratin etc. including the peptide polymer used in examples of present invention are preferable.

Preferable polysaccharide polymers are any one which can be mixed with cosmetic; however, hydroxy ethyl cellulose, xanthin gum, hyaluronic acid Na, chondroitin sulfate or their salt (Na salt etc) and the like are preferable. For example, chondroitin sulfate or the salt thereof etc can be used by being purified from mammal or fishes ordinarily.

Preferable sphingolipid are any one which can be mixed with cosmetic, however, ceramide, pit-sphingosin, sphingolipopolysaccharide and the like are preferable. Sphingo-lipid can be obtained by being purified from mammal, fish, shellfish, yeast or plant etc in conventional method.

Preferable seaweed extract is any one which can be mixed with cosmetic, however, the extract of brown algae, red algae, green algae and the like or the purified carrageenan, alginic acid, arginic acid Na, K isolated therefrom are preferable. Algae extract can be obtained by being purified from seaweed in conventional method.

The cosmetic composition of the present invention may combine with other ingredients used in conventional cosmetic composition, if necessary, together with above described essential ingredient.

Preferable above described other ingredients may comprise oil ingredient, humectants, emollients, surfactants, organic or inorganic dye, organic powder, ultraviolet ray absorbing agent, preservatives, antiseptics, antioxidants, plant extract, pH controller, alcohol, pigments, perfumes, refrigerants, blood circulator, antihidrotic, distilled water etc.

Preferable oil ingredients may comprise ester oil, hydrocarbon oil, silicone oil, fluoride oil, animal oil, plant oil and so on.

Preferable ester oil described above may comprise glyceryl tri-2-ethyl hexanoic acid, cetyl 2-ethyl hexanoic acid, isopropyl myristic acid, butyl myristic acid, isopropyl palmitic acid, ethyl stearic acid, octyl palmitic acid, isocetyl isostearic acid, butyl stearic acid, ethyl linoleic acid, isopropyl linoleic acid, ethyl oleic acid, isocetyl myristic acid, isostearyl myristic acid, isostearyl palmitic acid, octyldodecyl myristic acid, isocetyl isostearic acid, diethyl sebasic acid, isopropyl adipic acid, isoalkyl neopetanoic acid, glyceryl tri(capryl, capric acid), trimethylopropane tri-2-ethyl hexanoic acid, trimethylopropane triisostearic acid, pentaerythritol tetra-2 ethyl hexanoic acid, cetyl caprylic acid, decyl lauric acid, hexyl lauric acid, decyl myristic acid, myristyl myristic acid, cetyl myristic acid, stearyl stearic acid, decyl oleic acid, cetyl licinoleic acid, isostearyl lauric acid, isotridecyl myristic acid, isocetyl palmitic acid, octyl stearic acid, isocetyl stearic acid, isodecyl oleic acid, octyldodecyl oleic acid, octyldodecyl linoleic acid, isopropyl isostearic acid, cetostearyl 2-ethyl hexanoic acid, stearyl 2-ethyl hexanoic acid, hexyl isostearic acid, ethylene glycol dioctanoic acid, ethylene glycol dioleic acid, propylene glycol dicapric acid, propylene glycol di(capryl, capric acid), propylene glycol dicaprylic acid, neopentylglycol dicapric acid, neopentylglycol dioctanoic acid, glyceryl tricaprylic acid, glyceryl triundecylic acid, glyceryl triisopalmitic acid, glyceryl triisostearic acid, octyldodecyl neopentanoic acid, isostearyl octanoic acid, octyl isononanoic acid, hexyldecyl neodecanoic acid, octyldodecyl neodecanoic acid, isocetyl isostearic acid, isostearyl isostearic acid, octyldecyl isostearic acid, polyglycerin oleanoic acid ester, polyglycerin isostearic acid ester, triisocetyl citric acid, triisoalkyl citric acid, triisooctyl citric acid, lauryl lactic acid, myristyl lactic acid, cetyl lactic acid, octyldecyl lactic acid, triethyl citric acid, acetyltriethyl citric acid, acetyl tributyl citric acid, trioctyl citric acid, diisostearyl maleic acid, di 2-ethylhexyl hydroxy stearic acid, 2-ethyl hexyl succinic acid, diisobutyl adipic acid, diisopropyl sebasinic acid, dioctyl sebacinic acid, cholesteryl stearic acid, cholesteryl isostearic acid, cholesteryl hydroxy stearic acid, cholesteryl hydroxy stearic acid, cholesteryl oleic acid, dihydrocholesteryl oleic acid, pitsteryl isostearic acid, pitsteryl oleic acid, isocetyl 12-stealoyl hydroxy stearic acid, stearyl 12-stealoyl hydroxy stearic acid, isostearyl 12-stealoyl hydroxy stearic acid.

Preferable hydrocarbon oil described above may comprise squalene, liquid paraffin, α-olefin oligomer, isoparaffin, ceresin, paraffin, liquid isoparaffin, polybuden, micro-crystalline wax, vaselin and the like.

Preferable silicone oil may comprise polymethylsilicone, methylphenylsilicone, methylcyclopolysiloxane, octamethylpolysiloxane, decamethylpolysiloxane, dodecamethylcyclosiloxane, dimethyl siloxane-methyl cetyloxysiloxan copolymer, dimethyl siloxane-methyl stealoxysiloxane copolymer, alkyl modified silicone oil, amino modified silicone oil and the like.

Preferable fluoride oil can comprise perfluoropolyether and the like.

Preferable animal or plant oil can comprise avocado oil, almond oil, olive oil, sesame oil, rice husk oil, safflower oil, soy-bean oil, corn oil, rape oil, amygdalin oil, palm kernel oil, palm oil, pimaja oil, sunflower oil, fruite seed oil, cotton seed oil, coconut palm oil cucui nut oil, wheat embryo bud oil, rice embryo bud oil, sia butter, evening-primrose oil, marker daymia nut oil, medo home oil, egg yolk oil, lanolin, hempseed oil, mink oil, orange ruppy oil, hohoba oil, carnawa wax, liquid lanolin, solid pimaja wax and the like.

Preferable humectants can comprise water-soluble low molecular humectants, lipophilic low molecular humectants, water-soluble polymer and lipid soluble polymer. Specifically, preferable water soluble low molecular humectants can comprise cerin, glutamine, sorbitol, mannitol, pyrrolidonecarboxylic acid Na, glycerin, propylene glycol, 1,3-butylene glycol, ethylene glycol, polyethylene glycol (polymerization index. >2), polypropylene glycol (polymerization index >2), lactic acid, lactate salt, and the like.

Preferable lipid soluble low molecular humectants can comprise cholesterol, cholesteryl ester and the like.

Preferable water soluble polymer can comprise carboxy vinyl polymer, poly asparaginic acid salt, tragacanth, xanthin gum, HMC (hydroxy methyl celluose), HEC (hydroxy ethyl celluose), HPC (hydroxy propyl celluose), carboxymethylcellulose, water soluble chitin, chitosan, dextrin and the like.

Preferable lipid soluble polymer can comprise polyvinylpyrrolidone-eicocene copolymer, polyvinylpyrrolidonehexadecene copolymer, nitrocellulose, dextrin fatty acid ester, silicone polymer and the like.

Preferable emollients can comprise long chain acyl glutamic acid cholesteryl ester, cholesteryl hydroxy stearic acid, 12-hydroxy stearic acid, rogic acid, lanolin fatty acid cholesteryl ester and the like.

Preferable surfactant can comprise nonionic surfactants, anionic surfactants, cationic surfactants, ambivalent surfactants and the like.

Specifically, preferable non-ionic surfactants can comprise self-emulsified monostearic acid glycerin, propylene glycol fatty acid ester, glycerin fatty acid ester, polyglycerin fatty acid ester, sorbitan fatty acid ester, polyoxyethylene (POE) sorbitan fatty acid ester, POE sorbitan fatty acid ester, POE glycerin fatty acid ester, POE alkyl ether, POE fatty acid ester, POE solid pimaja oil, POE pimaja oil, POE-POP copolymer, POE-POP alkyl ether, polyether modified silicone, lauric acid alkanol amide, alkyl amine oxide, hydrogen addition soybean phospholipid and the like.

Preferable anionic surfactants can comprise fatty acid soap, a-acyl sulfonic acid salt, alkyl sulfonic acid salt, alkyl ally sulfonic acid, alkyl naphthalene sulfonic acid salt, alkyl sulfonic acid salt, POE alkylether sulfate salt, alkyl amide sulfate salt, alkyl phosphate salt, POE alkyl phosphate salt, alkylamide phosphate salt, alkyloylalkyl taurine salt, N-acyl-amino acid salt, POE alkyl ether carboxylic acid salt, alkyl sulfo succinic aid salt, alkyl sulfo-acetic acid salt, acylated hydrolysable collagen peptide salt, perfluoro alkyl phosphate ester and the like.

Preferable cationic surfactant can comprise alkyl trimethyl ammonium chloride, stearyl trimethyl ammonium chloride, stearyl trimethyl ammonium bromide, setostearyltrimethyl ammonium chloride, distearyl dimethyl ammonium chloride, stearyl dimethyl benzyl ammonium chloride, vehenyltrimethyl ammonium bromide, benzalkonium chloride, diethylamino ethyl amide stearic acid, dimethylaminopropyl amide stearic acid, lanolin derivatives quaternary ammonium and the like.

Preferable ambivalent surfactants can comprise carboxy betaine type, amide betaine type, hydroxy sulfo betaine type, phosphobetaine type, aminocarboxylic acid, imidazoline derivatives type, amide amine type and the like.

Preferable organic and inorganic dyes can comprise silicic acid, anhydrous silicic acid, magnesium silicic acid, talc, ceracyte, mica, caolin, bengala, clay, bentonite, titan film mica, oxy chlorine bismuth, zirconium oxide, magnesium oxide, zinc oxide, titan oxide, aluminium oxide, calcium sulfate, barium sulfate, magnesium sulfate, calcium carbonate, magnesium carbonate, ferrous oxide, chromium oxide, chromium hydroxide, calamine, carbon black and the complex thereof as an inorganic dyes; polyamide, polyester, polypropylene, polystyrene, polyurethane, vinyl resin, urea resin, phenol resin, fluoride resin, silicone resin, acryl resin, melamine resin, epoxy resin, polycarbonated resin, divinyl benzene-styrene copolymer, silk powder, cellulose, CI pigment yellow, CI pigment orange as an organic dyes; and their complex etc.

Preferable organic powder can comprise metal soap such as calcium stearate; alkyl phosphonate metal salt such as sodium zinc cetylic acid, zinc laurylic acid, calcium laurylic acid; acylamino acid polyvalent metal salt such as calcium N-lauroyl-b-alanine, zinc N-lauroyl-b-alanine, calcium N-lauroyl-glycine etc.; amide sulfonic acid polyvalent metal salt such as calcium N-lauroyl-taurine, calcium N-palmitoyl-taurine; N-acyl basic amino acid such as Nαlauroyl-L-lysine, Nαpalmitoyl-lysine, Na-palmitoyl ornitine, Na-lauroly arginine, hardened lanolin fatty acid acyl arginine and the like; N-acylpolypeptide such as N-lauroylglycyl glycine; a-amino fatty acid such as a-amino caprylic acid, a-amino lauric acid and the like; polyethylene, polypropylene, nylon, polymethylmetacrylate, polystyrene, divinylbenzene-styrene copolymer, ethylene tetrafluoride and so on.

Preferable ultraviolet absorbing agents can comprise paraminobenzoic acid, paraamonoethyl benzoate, paramino amyl benzoate, paramino octyl benzoate, ethyleneglycol salicylate, phenyl salicylate, octyl salicylate, benzyl salicylate, butylphenyl salicylate, homomentyl salicylate, benzyl cinnamic acid, paramethoxy 2-ethoxy ethyl cinnamic acid, paramethoxy octyl cinnamic acid, diparamethoxy mono-2-ethylhexane glyceryl cinnamic acid, paramethoxy isopropyl cinnamic acid, diisopropyl-diisopropyl cinnamate ester mixture, urokanic acid, ethyl urokanic acid, hydroxy methoxy benzophenone, hydroxymethoxy benzophenone sulfonic acid and their salt, dihydroxy methoxy benzophenone, dihydroxy methoxy benzophenone disulfonate Na, dihydroxy benzophenone, tetrahydroxybenzophenone, 4-tert-butyl-4'-methoxydibenzoylmethane, 2,4,6-trianilino-p-(carbo-2'-ethylhexyl-1'-oxy)-1,3,5-triazine, 2-(2-hydroxy-5-methylphenyl) benzotriazole and the like.

Preferable preservatives can comprise hinokitiol, trichloric acid, trichlorohydroxy-diphenylether, chlorohexidine glucuronate, phenoxyethanol, resorcine, isopropyl-methylphenol, azulene, salicylic acid, zinc pilithione, bezalconium HCl, photo-sensitizer 301, mononitroguaiacol Na, undecylenic acid etc.

Preferable antioxidants can comprise butylhydroxyanisole, propyl gallate, ellisorbate and the like.

Preferable pH controller can comprise citric acid, sodium citrate, malic acid, sodium malate, fumaric acid, sodium fumaric acid, succinic acid, sodium succinic acid, sodium hydroxide, sodium hydrogen phosphate and the like.

Preferable alcohol can comprise cetyl alcohol etc.

Furthermore, other ingredient addable to above described component and the amount thereof is not limited within the scope of the purpose and effect of the present invention, however, it is preferable that the amount of the other ingredients ranges from 0.01 to 5%, more preferably, 0.01 to 3% in that of total composition.

The cosmetic composition of the present invention can be modified as a solution, emulsion, cohesive mixture etc.

Above described ingredients such as water-soluble vitamin, lipid soluble vitamin, peptide polymer, polysaccharide polymer, sphingolipid, sea weed extract and addable ingredients which can be added other than above described ingredients if necessary, can be obtained by conventional methods disclosed in the literature (Matsumoto Mithio; Manual for the development of transdermal applied preparation. Seisi Press, $1^{st}$ Ed., 1985).

Inventive compounds of the present invention have no toxicity and adverse effect therefore; they can be used with safe.

It will be apparent to those skilled in the art that various modifications and variations can be made in the compositions, use and preparations of the present invention without departing from the spirit or scope of the invention.

Advantageous Effects

Novel derivatives of cyclic compound have potent inhibiting effect on melanin formation and skin hyper-pigmentation activity with no adverse response to skin, therefore, they can be used as the therapeutics for treating and preventing the skin disease caused by over-reproduced melanin.

BEST MODE FOR CARRYING OUT THE INVENTION

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

MODE FOR THE INVENTION

The following Examples, Experimental Example, Preparation Examples, and Clinical Example are intended to further illustrate the present invention without limiting its scope.

Example 1

Preparation of butyric acid 2-butyryloxy-trans-cyclohexyl ester Compound (1)

After adding 1.16 g of trans-1,2-cyclohexandiol (10 mmol) into 2 neck round flask at room temperature, 50 ml of dichloromethane was added thereto, and the mixture was cooled using by ice bath. Both 0.24 g of dimethylaminopyridine (2 mmol) and 2.3 g of triethylamine (23 mmol) were added thereto as a catalyst and 2.3 g of butyryl chloride (22 mmol) was added thereto slowly. The mixture was reacted for 2 hrs at room temperature after finishing the addition of the butyryl chloride. After adding 100 ml of watery hydrochloric acid to the reaction mixture, the mixture was extracted with 200 ml of dichloromethane. The dichloromethane layer was dried under reduced pressure and separated by column chromatography on Silica gel with EtOAc/hexanes (1:30) solvent mixture as an eluant to give 2.6 g of butyric acid 2-butyryloxy-trans-cyclohexyl ester. The obtained butyric acid 2-butyryloxy-trans-cyclohexyl ester was purified using by FAB-MS (fast atom bombardment-mass spectrometry) and $^1$H-NMR to obtain 1.8 g of purified butyric acid 2-butyryloxy-trans-cyclohexyl ester.

FAB mass: 257 [M+H]$^+$ $^1$H-NMR (CDCl$_3$, 300 MHz): 0.93(t, 6H, J=7.5 Hz), 1.25~1.45(m, 4H), 1.62(h, 4H, J=7.5 Hz), 1.64~1.75(m, 2H), 1.95~2.10(m, 2H), 2.24(t, 4H, J=7.5 Hz), 4.77~4.86(m, 2H)

Example 2

Preparation of pentanoic acid 2-pentanoyloxy-trans-cyclohexyl ester Compound (2)

The compound 2 was prepared by the same procedure with the method described in Example 1 excepting using pentanoyl chloride instead of butyryl chloride to give 2.1 g of pentanoic acid 2-pentanoyloxy-trans-cyclohexyl ester.

*FAB mass: 285 [M+H]$^+$ $^1$H-NMR (CDCl$_3$ 300 MHz): 0.93(t, 6H, J=7.5 Hz), 1.25~1.45(m, 4H), 1.34(h, 4H, J=7.2), 1.58(q, 4H, J=7.2 Hz), 1.64~1.75(m, 2H), 1.95~2.06(m, 2H), 2.26(t, 4H, J=7.5 Hz), 4.85~4.93(m, 2H)

Example 3

Preparation of 3-methyl-2-butenoic acid 2-(3-methyl-2-butenoyloxy)-trans-cyclohexyl ester Compound (3)

The compound 3 was prepared by the same procedure with the method described in above Example 1 excepting using 3-methyl-2-butenoyl chloride instead of butyryl chloride to give 2.11 g of 3-methyl-2-butenoic acid 2-(3-methyl-2-butenoyloxy)-trans-cyclohexyl ester.

FAB mass: 281 [M+H]$^+$ $^1$H-NMR (CDCl$_3$, 300 MHz): 1.30~1.45(m, 4H), 1.66~1.75(m, 2H), 1.87(s, 3H), 2.01~2.12(m, 2H), 2.23(s, 3H), 4.85~4.93(m, 2H), 5.63(s, 2H)

Example 4

Preparation of hexanoic acid 2-hexanoyloxy-trans-cyclohexyl ester Compound (4)

The compound 4 was prepared by the same procedure with the method described in above Example 1 excepting using hexanoyl chloride instead of butyryl chloride to give 2.2 g of hexanoic acid 2-hexanoyloxy-trans-cyclohexyl ester.

FAB mass: 313 [M+H]$^+$ $^1$H-NMR (CDCl$_3$, 300 MHz): 0.89(t, 6H, J=6.9 Hz), 1.20~1.45(m, 8H), 1.59((q, 4H, J=7.5 Hz), 1.66~1.75(m, 2H), 1.95~2.15(m, 2H), 2.28(t, 4H, J=8.1 Hz), 4.85~4.95(m, 2H)

Example 5

Preparation of heptanoic acid 2-heptanoyloxy-trans-cyclohexyl ester Compound (5)

The compound 5 was prepared by the same procedure with the method described in above Example 1 excepting using heptanoyl chloride instead of butyryl chloride to give 2.3 g of heptanoic acid 2-heptanoyloxy-trans-cyclohexyl ester.

FAB mass: 341 [M+H]$^+$ $^1$H-NMR (CDCl$_3$, 300 MHz): 0.88(t, 6H, J=6.9 Hz), 1.20~1.45(m, 10H), 1.58(q, 4H, J=7.2 Hz), 1.66~1.75(m, 2H), 1.95~2.15(m, 2H), 2.25(t, 2H, J=7.5 Hz), 2.26(t, 2H, J=7.2 Hz), 4.85~4.95(m, 2H)

Example 6

Preparation of octanoic acid 2-octanoyloxy-trans-cyclohexyl ester Compound (6)

The compound 6 was prepared by the same procedure with the method described in above Example 1 excepting using octanoyl chloride instead of butyryl chloride to give 2.5 g of octanoic acid 2-octanoyloxy-trans-cyclohexyl ester.

FAB mass: 369 [M+H]$^+$ $^1$H-NMR (CDCl$_3$, 300 MHz): 0.88(t, 6H, J=6.9 Hz), 1.20~1.45(m, 12H), 1.58(q, 4H, J=6.9 Hz), 1.66~1.75(m, 2H), 1.95~2.15(m, 2H), 2.25(t, 2H, J=7.5 Hz), 2.26(t, 2H, J=7.8 Hz), 4.85~4.95(m, 2H)

Example 7

Preparation of 2-ethyl-hexanoic acid 2-(2-ethyl-hexanoyloxy)-trans-cyclohexyl ester Compound (7)

The compound 7 was prepared by the same procedure with the method described in above Example 1 excepting using 2-ethyl-hexanoyl chloride instead of butyryl chloride to give 2.4 g of 2-ethyl-hexanoic acid 2-(2-ethyl-hexanoyloxy)-trans-cyclohexyl ester.

FAB mass: 369 [M+H]$^+$ $^1$H-NMR (CDCl$_3$, 300 MHz): 0.88(t, 6H, J=6.9 Hz), 0.94 (t, 6H, J=7.5 Hz), 1.20~1.40(m, 10H), 1.40~1.70(m, 8H), 2.05~2.15(m, 2H), 2.15~2.35(m, 4H) 4.85~4.95(m, 2H)

Example 8

Preparation of nonanoic acid 2-nonanoyloxy-trans-cyclohexyl ester Compound (8)

The compound 8 was prepared by the same procedure with the method described in above Example 1 excepting using nonanoyl chloride instead of butyryl chloride to give 2.8 g of nonanoic acid 2-nonanoyloxy-trans-cyclohexyl ester.

FAB mass: 397 [M+H]$^+$ $^1$H-NMR (CDCl$_3$, 300 MHz): 0.88(t, 6H, J=6.9 Hz), 1.20~1.45(m, 14H), 1.58(q, 4H, J=7.2 Hz), 1.66~1.75(m, 2H), 1.95~2.15(m, 2H), 2.25(t, 2H, J=7.5 Hz), 2.26(t, 2H, J=7.5 Hz), 4.85~4.95(m, 2H)

Example 9

Preparation of decanoic acid 2-decanoyloxy-trans-cyclohexyl ester Compound (9)

The compound 9 was prepared by the same procedure with the method described in above Example 1 excepting using decanoyl chloride instead of butyryl chloride to give 3.1 g of decanoic acid 2-decanoyloxy-trans-cyclohexyl ester.

FAB mass: 425 [M+H]$^+$
$^1$H-NMR (CDCl$_3$, 300 MHz): 0.88(t, 6H, J=6.9 Hz), 1.20~1.45(m, 16H), 1.58(q, 4H, J=6.9 Hz), 1.66~1.75(m, 2H), 1.95~2.15(m, 2H), 2.25(t, 2H, J=7.5 Hz), 2.26(t, 2H, J=7.8 Hz), 4.85~4.95(m, 2H)

Example 10

Preparation of lauric acid 2-lauroyloxy-trans-cyclohexyl ester Compound (10)

The compound 10 was prepared by the same procedure with the method described in above Example 1 excepting using lauroyl chloride instead of butyryl chloride to give 3.2 g of lauric acid 2-lauroyloxy-trans-cyclohexyl ester.

FAB mass: 481 [M+H]$^+$
$^1$H-NMR (CDCl$_3$, 300 MHz): 0.85(t, 6H, J=6.4 Hz), 1.22~1.33(m, 34H), 1.52~1.59(q, 4H, J=6.4 Hz), 1.67~1.69 (m, 2H), 1.98~2.01(m, 2H), 2.14~2.19(t, 2H, J=7.5 Hz), 2.26 (t, 2H, J=8.2 Hz), 4.4.76~4.79(m, 2H)

Example 11

Preparation of 3-methyl-2-butenoic acid 2-(3-methyl-2-butenoyloxy)-cis-cyclohexyl ester Compound (11)

The compound 11 was prepared by the same procedure with the method described in above Example 3 excepting using cis-1,2-cyclohexandiol instead of trans-1,2-cyclohexandiol to give 1.5 g of 3-methyl-2-butenoic acid 2-(3-methyl-2-butenoyloxy)-cis-cyclohexyl ester.

FAB mass: 281 [M+H]$^+$
$^1$H-NMR (CDCl$_3$, 300 MHz): 1.25~1.5(m, 4H), 1.61~1.72 (m, 6H), 1.81~1.92(m, 6H), 2.11~2.19(m, 4H), 5.04~5.07(d, 2H, J=7.8 Hz), 5.67~5.68(d, 2H, J=1.2 Hz)

Example 12

Preparation of 3-methyl-2-butenoic acid 2-(3-methyl-2-butenoyloxy)-trans-cyclopentyl ester Compound (12)

The compound 12 was prepared by the same procedure with the method described in above Example 3 excepting using trans-1,2-cyclopentandiol instead of trans-1,2-cyclohexandiol to give 1.6 g of 3-methyl-2-butenoic acid 2-(3-methyl-2-butenoyloxy)-trans-cyclopentyl ester.

*FAB mass: 267.1[M+H]$^+$
$^1$H-NMR (CDCl$_3$, 300 MHz): 1.64~1.69(m, 2H), 1.75~1.80(m, 2H), 2.05~2.15(m, 2H), 1.88(s, 6H), 2.15(s, 6H), 5.09~5.12(m, 2H), 5.65~5.66(d, 2H, J=1.2 Hz)

Example 13

Preparation of octanoic acid 2-octanoyloxy-trans-cyclopentyl ester Compound (13)

The compound 13 was prepared by the same procedure with the method described in above Example 6 excepting using trans-1,2-cyclopentandiol instead of trans-1,2-cyclohexandiol to give 1.8 g of octanoic acid 2-octanoyloxy-trans-cyclopentyl ester.

FAB mass: 355.2 [M+H]$^+$
$^1$H-NMR (CDCl$_3$, 300 MHz): 0.88(m, 6H), 1.22~1.38(m, 20H), 1.58~1.62(m, 6H), 1.74~1.79(m, 2H), 2.07~2.12(m, 2H), 2.25~2.30(t, 4H, J=6.6 Hz), 5.07~5.08(m, 2H)

Example 14

Preparation of 2-ethyl-hexanoic acid 2-(2-ethyl-hexanoyloxy)-trans-cyclopentyl ester Compound (14)

The compound 14 was prepared by the same procedure with the method described in above Example 7 excepting using trans-1,2-cyclopentandiol instead of trans-1,2-cyclohexandiol to give 1.7 g of 2-ethyl-hexanoic acid 2-(2-ethyl-hexanoyloxy)-trans-cyclopentyl ester.

FAB mass: 355.2 [M+H]$^+$
$^1$H-NMR (CDCl$_3$, 300 MHz): 0.85~0.90(m, 12H), 1.23~1.33(m, 8H), 1.40~1.66(m, 10H), 1.66~1.84(m, 2H), 2.08~2.30(m, 4H), 5.08~5.09(m, 2H)

Example 15

Preparation of 4-pentenoic acid 2-(4-pentenoyloxy)-trans-cyclohexyl ester Compound (15)

The compound 15 was prepared by the same procedure with the method described in above Example 1 excepting using 4-pentenoyl chloride instead of butyryl chloride to give 1.8 g of 4-pentenoic acid 2-(4-pentenoyloxy)-trans-cyclohexyl ester.

FAB mass: 281.1 [M+H]$^+$
$^1$H-NMR (CDCl$_3$, 300 MHz): 1.20~1.45(m, 4H), 1.65~1.80(m, 2H), 1.95~2.10(m, 2H), 2.30~2.45(m, 8H), 4.80~4.90(m, 2H), 4.99(d, 2H, J=11.7 Hz), 5.04(dd, 2H, J=0.6 Hz, J=11.7 Hz), 5.85~5.95(m, 2H)

Example 16

Preparation of 3-methyl-2-butenoic acid 2-(3-methyl-2-butenoyloxy)-phenyl ester Compound (16)

The compound 16 was prepared by the same procedure with the method described in above Example 3 excepting using 1,2-benzendiol instead of trans-1,2-cyclohexandiol to give 1.8 g of 3-methyl-2-butenoic acid 2-(3-methyl-2-butenoyloxy)-phenyl ester.

FAB mass: 275 [M+H]$^+$
$^1$H-NMR (CDCl$_3$, 300 MHz): 1.99(s, 6H), 2.22(s, 6H), 5.89~5.91(m, 2H), 7.18~7.28(m, 4H)

Example 17

Preparation of octanoic acid 2-octanoyloxy-phenyl ester Compound (17)

The compound 17 was prepared by the same procedure with the method described in above Example 6 excepting using 1,2-benzendiol instead of trans-1,2-cyclohexandiol to give 2.3 g of octanoic acid 2-octanoyloxy-phenyl ester.

FAB mass: 363.1 [M+H]$^+$
$^1$H-NMR (CDCl$_3$, 300 MHz): 0.88~0.93(m, 6H), 1.32~1.46(m, 16H), 1.70~1.80(m, 4H), 2.52~2.57(m, 4H), 7.02~7.18(m, 4H)

Example 18

Preparation of 3-methyl-2-butenoic acid 3-(3-methyl-2-butenoyloxy)-naphthalen-2-yl ester Compound (18)

The compound 18 was prepared by the same procedure with the method described in above Example 3 excepting using 2,3-naphthalendiol instead of trans-1,2-cyclohexandiol to give 2.5 g of 3-methyl-2-butenoic acid 3-(3-methyl-2-butenoyloxy)-naphthalen-2-yl ester.

FAB mass: 324.9 $[M+H]^+$
$^1$H-NMR (CDCl$_3$, 300 MHz): 1.97(d, 6H, J=1.29 Hz), 2.20(d, 6H, J=1.29 Hz), 5.90~5.92(m, 2H), 7.41~7.45(m, 2H), 7.63(s, 2H), 7.75~7.78(m, 2H)

Example 19

Preparation of octanoic acid 3-octanoyloxy-naphthalen-2-yl ester Compound (19)

The compound 19 was prepared by the same procedure with the method described in above Example 6 excepting using 2,3-naphthalendiol instead of trans-1,2-cyclohexandiol to give 2.5 g of octanoic acid 3-octanoyloxy-naphthalen-2-yl ester.

FAB mass: 413 $[M+H]^+$
$^1$H-NMR (CDCl$_3$, 300 MHz): 0.86~0.91 (m, 6H), 1.30~1.39(m, 16H), 1.71~1.81(m, 4H), 2.54~2.59(m, 4H), 7.43~7.46(m, 2H), 7.62(s, 2H), 7.75~7.78(m, 2H)

Example 20

Preparation of 2-ethyl-hexanoic acid 3-(2-ethyl-hexanoyloxy)-naphthalen-2-yl ester Compound (20)

The compound 20 was prepared by the same procedure with the method described in above Example 7 excepting using 2,3-naphthalendiol instead of trans-1,2-cyclohexandiol to give 2.3 g of 2-ethyl-hexanoic acid 3-(2-ethyl-hexanoyloxy)-naphthalen-2-yl ester.

FAB mass: 413 $[M+H]^+$
$^1$H-NMR (CDCl$_3$, 300 MHz): 0.85~1.06(m, 12H), 1.29~1.39(m, 10H), 1.53~1.83(m, 10H), 2.31~2.37(m, 2H), 2.49~2.58(m, 2H), 7.42~7.47(m, 2H), 7.61(s, 2H), 7.75~7.78 (m, 2H)

Example 21

Preparation of octanoic acid 3-octanoyloxy-pyridin-2-yl ester Compound (21)

The compound 21 was prepared by the same procedure with the method described in above Example 7 excepting using 2,3-pyridindiol instead of trans-1,2-cyclohexandiol to give 1.2 g of octanoic acid 3-octanoyloxy-pyridin-2-yl ester.

FAB mass: 364.1 $[M+H]^+$
$^1$H-NMR (CDCl$_3$, 300 MHz): 0.81~0.85(m, 6H), 1.25~1.37(m, 16H), 1.56~1.75(m, 4H), 2.54~2.59(m, 4H), 6.22~6.26(t, 2H, J=6.75 Hz), 7.21~7.23(m, 1H)

Example 22

Preparation of 3-methyl-2-butenoic acid 4-(3-methyl-2-butenoyloxy)-tetrahydrofuran-3-yl ester Compound (22)

The compound 22 was prepared by the same procedure with the method described in above Example 3 excepting using 3,4-tetrahydrofurandiol instead of trans-1,2-cyclohexandiol to give 1.6 g of 3-methyl-2-butenoic acid 4-(3-methyl-2-butenoyloxy)-tetrahydrofuran-3-yl ester.

FAB mass: 269.1 $[M+H]^+$
$^1$H-NMR (CDCl$_3$, 300 MHz): 1.91~2.15(m, 12H), 2.15~2.17(m, 6H), 3.80~3.86(m, 2H), 4.07~4.08(m, 2H), 4.85~4.91(m, 1H), 5.34~5.38(m, 2H), 5.68~5.69(m, 1H)

Example 23

Preparation of butyric acid 3-methyl-2-butenoic acid 2,3-bis-(3-methyl-2-butenoyloxy)-phenyl ester Compound (23)

After adding 1.26 g of 1,2,3-benzenetriol (10 mmol) into 2 neck round flask at room temperature, 50 ml of dichloromethane was added thereto, and the mixture was cooled using by ice bath. Both 0.36 g of dimethylaminopyridine (2 mmol) and 3.6 g of tri-ethylamine (36 mmol) were added thereto as a catalyst and 3.5 g of 3-methyl-2-butenoyl chloride (33 mmol) was added thereto slowly. The mixture was reacted for 2 hrs at room temperature after the ending of the addition of 3-methyl-2-butenoyl chloride. After adding 100 ml of watery hydrochloric acid to the reaction mixture, the mixture was extracted with 200 ml of dichloromethane. The dichloromethane layer was dried under reduced pressure, separated, and purified by column chromatography on Silica gel with EtOAc/hexane (1:10) solvent mixture as an eluant to give 3.2 g of butyric acid 3-methyl-2-butenoic acid 2,3-bis-(3-methyl-2-butenoyloxy)-phenyl ester.

FAB mass: 373 $[M+H]^+$
$^1$H-NMR (CDCl$_3$, 300 MHz): 1.93(s, 9H), 2.17(s, 9H), 5.82~5.85(m, 3H), 7.17(s, 1H), 7.20~7.21(m, 1H), 7.23~7.24 (m, 1H)

Example 24

Preparation of octanoic acid 2,3-bis-octanoyloxy-cyclohexyl ester Compound (24)

The compound 24 was prepared by the same procedure with the method described in above Example 23 excepting using 1,2,3-cyclohexanetriol instead of 1,2,3-benzenetriol to give 2.9 g of octanoic acid 2,3-bis-octanoyloxy-cyclohexyl ester.

FAB mass: 511 $[M+H]^+$
$^1$H-NMR (CDCl$_3$, 300 MHz): 0.82~0.87(m, 9H), 1.20~1.30(m, 24H), 1.50~1.65(m, 8H), 1.79~1.83(m, 1H), 1.99~2.04(m, 1H), 2.13~2.33(m, 6H), 4.90~4.94(m, 1H), 5.05~5.12(m, 1H), 5.31~5.33(m, 1H)

Example 25

Preparation of myo-inositol hexa-O-butanoate Compound (25)

After adding 1.8 g of myo-inositol (10 mmol) into 2 neck round flask at room temperature, 50 ml of pyridine was added thereto, and the mixture was dissolved using by water bath. After cooling the mixture using by ice bath, the mixture was treated by dropwise addition of six-equivalents of anhydrous butanoic acid, stirred, and treated by dropwise addition of more six-equivalents of anhydrous butanoic acid. The mixture was reacted for 48 hrs at room temperature. The reaction was stopped by adding 100 ml of methanol, the solvent was removed under reduced pressure, and 200 ml of chloroform was added thereto. The mixture was washed 2 times with 200 ml of 1N aqueous solution of hydrogen chloride and 200 ml of saturated solution of sodium carbonate. The chloroform layers were dried under reduced pressure and purified by column chromatography on Silica gel with EtOAc/hexane (1:10) solvent mixture as an eluant to give 0.9 g of myo-inositol hexa-O-butanoate.

FAB mass: 623 [M+Na]$^+$
$^1$H-NMR (CDCl$_3$, 300 MHz): 0.82~0.92(m, 18H), 1.85~2.13(m, 12H), 2.13~2.31(m, 12H), 5.09~5.10(d, 1H, J=2.9 Hz), 5.12~5.13(d, 1H, J=2.9 Hz), 5.17~5.22(t, 1H, 9.2 Hz), 5.48~5.54(t, 2H, 9.2 Hz), 5.61~5.62(t, 1H, J=2.9 Hz)

Example 26

Preparation of Arabinopyranose 1,2,3,4-tetra-O-(3-methyl-2-butenoate Compound (26)

The compound 26 was prepared by the same procedure with the method described in above Example 25 excepting using arabinopyranose instead of myo-inositol to give 0.8 g of arabinopyranose 1,2,3,4-tetra-O-(3-methyl-2-butenoate.

FAB mass: 501.1 [M+Na]$^+$
$^1$H-NMR (CDCl$_3$, 300 MHz): 1.93~1.95(m, 12H), 2.13~2.22(m, 12H), 3.16~3.18(m, 2H), 4.35~4.45(m, 1H), 4.82~4.95(m, 3H), 5.78~5.92(m, 4H)

Example 27

Preparation of methyl-alpha-D-glucose tetra-O-butanoate Compound (27)

The compound 27 was prepared by the same procedure with the method described in above Example 25 excepting using methyl-alpha-D-glucose instead of myo-inositol to give 0.7 g of methyl-alpha-D-glucose tetra-O-butanoate.

FAB mass: 497 [M+Na]$^+$
$^1$H-NMR (CDCl$_3$, 300 MHz): 0.87~0.92(m, 12H), 1.93~2.15(m, 8H), 2.15~2.31(m, 8H), 3.27(s, 3H), 3.92~3.93 (m, 1H), 4.10~4.11 (m, 1H), 4.28~4.29(m, 1H), 4.87~4.88 (m, 1H), 4.93~4.94(d, 1H, J=6.2 Hz), 5.05~5.06(m, 1H), 5.48~5.49(m, 1H)

Example 28

Preparation of 1,2-bis-(3-methyl-buthoxy)-cyclohexane Compound (28)

After adding 1.6 g of sodium hydride (60%, 40 mmol) and 200 ml of anhydrous tetrahydrofuran into 500 ml volume of 3 neck round flask equipped with a thermometer and a condenser, the mixture was stirred at room temperature and 2.32 g of trans-1,2-cyclohexanediol of solid state (20 mmol) was added thereto. The mixture was stirred for 30 mins. After adding 5.50 g of 3-methyl-butyl bromide thereto, the mixture was stirred for over 36 hrs at reflux temperature of tetrahydrofuran and 100 ml of water was added to the reaction mixture. The reaction mixture was extracted using by 200 ml of ether. The remaining solution was dried with anhydrous magnesium sulfate, filtered, concentrated, and purified by column chromatography on Silica gel with EtOAc/hexane (1:50) solvent mixture as an eluant to give 2.7 g of 1,2-bis-(3-methyl-buthoxy)-cyclohexane.

FAB mass: 257 [M+H]$^+$
$^1$H-NMR (CDCl$_3$, 300 MHz): 0.86(s, 6H), 0.88(s, 6H), 1.12~1.18(m, 4H), 1.36~1.50(m, 4H), 1.60~1.75(m, 4H), 1.94~1.96(m, 2H), 3.08~3.10(m, 2H), 3.52~3.60(t, 4H, J=6.9 Hz)

Example 29

Preparation of 1,2-bis-pentyloxy-cyclohexane Compound (29)

The compound 29 was prepared by the same procedure with the method described in above Example 28 excepting using pentyl bromide instead of 3-methyl-butyl bromide to give 2.3 g of 1,2-bis-pentyloxy-cyclohexane.

FAB mass: 257 [M+H]$^+$
$^1$H-NMR (CDCl$_3$, 300 MHz): 0.84~0.92(m, 6H), 1.12~1.35(m, 12H), 1.48~1.67(m, 6H), 1.91~1.96(m, 2H), 3.08~3.10(m, 2H), 3.49~3.54(t, 4H, J=6.75 Hz)

Example 30

Preparation of 1,2-bis-hexyloxy-cyclohexane Compound (30)

The compound 30 was prepared by the same procedure with the method described in above Example 28 excepting using hexyl bromide instead of 3-methyl-butyl bromide to give 1.9 g of 1,2-bis-hexyloxy-cyclohexane.

FAB mass: 285 [M+H]$^+$
$^1$H-NMR (CDCl$_3$, 300 MHz): 0.83~0.87(m, 6H), 1.06~1.37(m, 18H), 1.47~1.66(m, 4H), 1.91~1.96(m, 2H), 3.08~3.10(m, 2H), 3.50~3.54(t, 4H, J=6.6 Hz)

Example 31

Preparation of 1,2-bis-octyloxy-cyclohexane Compound (31)

The compound 31 was prepared by the same procedure with the method described in above Example 28 excepting using hexyl bromide instead of 3-methyl-butyl bromide to give 2.1 g of 1,2-bis-octyloxy-cyclohexane.

FAB mass: 341.2 [M+H]$^+$
$^1$H-NMR (CDCl$_3$, 300 MHz): 0.82~0.87(m, 6H), 1.16~1.29(m, 26H), 1.47~1.62(m, 4H), 1.91~1.95(m, 2H), 3.08~3.10(m, 2H), 3.50~3.54(t, 4H, J=6.7 Hz)

Experimental Example 1

Inhibitory Effect on Melanin Synthesis

In order to confirm the inhibition effect of the compounds prepared in Examples 1 to 31 and hydroquinone on melanin biosynthesis, the experiment was performed with the procedure described in the literature (Lotan R., Lotan D. Cancer Res., 40, pp. 3345-3350, 1980).

After adding the compounds prepared in Examples 1 to 31 at the final concentration of 5 microgram/ml and 2 microgram/ml to the medium containing mouse melanoma B-16 cells respectively. The medium was cultured for 3 days and the cultured cells were separated from the medium by treating with trypsin. The separated cells were centrifuged and the melanin was extracted therefrom. The extract was treated with 1 ml of sodium hydroxide solution (1N) and boiled for 10 mins to resolve the melanin. Optical density (OD) value was measured 3 times at 475 nm by a spectrophotometer and the amount of melanin was expressed by absorbance(OD)/1×

$10^6$ cells. The inhibitory effect of melanin (%) was calculated from the melanin synthesis as compared with the control group.

TABLE 1

| Examples | Concentration (ug/ml) | Melanin synthesis inhibition (%) |
|---|---|---|
| Control group | — | — |
| Hydroquinone | 1 | 45 |
|  | 5 | Cell death |
| Example 1 | 5 | 30 |
|  | 20 | 55 |
| Example 2 | 5 | 45 |
|  | 20 | 78 |
| Example 3 | 5 | 39 |
|  | 20 | 72 |
| Example 4 | 5 | 41 |
|  | 20 | 71 |
| Example 5 | 5 | 35 |
|  | 20 | 56 |
| Example 6 | 5 | 30 |
|  | 20 | 51 |
| Example 7 | 5 | 42 |
|  | 20 | 69 |
| Example 8 | 5 | 21 |
|  | 20 | 47 |
| Example 9 | 5 | 19 |
|  | 20 | 39 |
| Example 10 | 5 | 9 |
|  | 20 | 15 |
| Example 11 | 5 | 31 |
|  | 20 | 54 |
| Example 12 | 5 | 27 |
|  | 20 | 56 |
| Example 13 | 5 | 30 |
|  | 20 | 54 |
| Example 14 | 5 | 31 |
|  | 20 | 57 |
| Example 15 | 5 | 39 |
|  | 20 | 72 |
| Example 16 | 5 | 15 |
|  | 20 | 27 |
| Example 17 | 5 | 9 |
|  | 20 | 18 |
| Example 18 | 5 | 47 |
|  | 20 | 67 |
| Example 19 | 5 | 39 |
|  | 20 | 61 |
| Example 20 | 5 | 29 |
|  | 20 | 55 |
| Example 21 | 5 | 48 |
|  | 20 | 81 |
| Example 22 | 5 | 27 |
|  | 20 | 49 |
| Example 23 | 5 | 48 |
|  | 20 | 75 |
| Example 24 | 5 | 39 |
|  | 20 | 69 |
| Example 25 | 5 | 27 |
|  | 20 | 59 |
| Example 26 | 5 | 31 |
|  | 20 | 61 |
| Example 27 | 5 | 29 |
|  | 20 | 49 |
| Example 28 | 5 | 25 |
|  | 20 | 49 |
| Example 29 | 5 | 22 |
|  | 20 | 43 |
| Example 30 | 5 | 18 |
|  | 20 | 41 |
| Example 31 | 5 | 15 |
|  | 20 | 31 |

As shown in Table 1, all compounds showed similar inhibitory activity of melanin synthesis in mouse B-16 melanoma cells to that of hydroquinone. The hydroquinone showed potent inhibitory activity at low concentration however it showed high levels of cytotoxicity. Therefore, the compounds of the present invention without cytotoxicity showed more potent inhibitory activity on melanin synthesis than hydroquinone used as a positive control.

Preparation Example 1

Preparation of Skin Lotion

The preparations were manufactured as described in following Table 2.

TABLE 2

| Composition (% of weight) | Preparation 1 | | | | Comparative preparation 1 |
|---|---|---|---|---|---|
|  | a | b | c | d | |
| Example 6 | 0.1 | — | — | — | — |
| Example 18 | — | 0.1 | — | — | — |
| Example 23 | — | — | 0.1 | — | — |
| Example 30 | — | — | — | 0.1 | — |
| Ethanol | 10.0 | 10.0 | 10.0 | 10.0 | 10.0 |
| Polyoxyethylene hydrogenated caster oil | 1.0 | 1.0 | 1.0 | 1.0 | 1.0 |
| Methyl parahydroxybenzoate | 0.2 | 0.2 | 0.2 | 0.2 | 0.2 |
| Glycerin | 5.0 | 5.0 | 5.0 | 5.0 | 5.0 |
| 1,3-butylene glycol | 6.0 | 6.0 | 6.0 | 6.0 | 6.0 |
| Flavor | trace amount | trace amount | trace amount | trace amount | trace amount |
| Distilled water | to 100 | to 100 | to 100 | to 100 | to 100 |

Preparation Example 2

Preparation of Lotion

The preparations were manufactured as described in following Table 3.

TABLE 3

| Composition (% of weight) | Preparation 2 | | | | Comparative preparation 2 |
|---|---|---|---|---|---|
|  | a | b | c | d | |
| Example 6 | 0.1 | — | — | — | — |
| Example 18 | — | 0.1 | — | — | — |
| Example 23 | — | — | 0.1 | — | — |
| Example 30 | — | — | — | 0.1 | — |
| Polyoxyethylene hydrogenated caster oil | 1.0 | 1.0 | 1.0 | 1.0 | 1.0 |
| Methyl parahydroxybenzoate | 0.2 | 0.2 | 0.2 | 0.2 | 0.2 |
| Glycerin | 6.0 | 6.0 | 6.0 | 6.0 | 6.0 |
| 1,3-butylene glycol | 5.0 | 5.0 | 5.0 | 5.0 | 5.0 |
| Carbomer | 0.2 | 0.2 | 0.2 | 0.2 | 0.2 |
| Triethanolamine | 0.3 | 0.3 | 0.3 | 0.3 | 0.3 |
| Propylene glycol | 5.0 | 5.0 | 5.0 | 5.0 | 5.0 |
| Ethanol | 3.2 | 3.2 | 3.2 | 3.2 | 3.2 |
| carboxyvinylpolymer | 0.1 | 0.1 | 0.1 | 0.1 | 0.1 |
| Flavor | trace amount | trace amount | trace amount | trace amount | trace amount |
| Distilled water | to 100 | to 100 | to 100 | to 100 | to 100 |

Preparation Example 3

Preparation of Cream

The preparations were manufactured as described in following Table 4.

TABLE 4

| Composition (% of weight) | Preparation 3 a | b | c | d | Comparative preparation 3 |
|---|---|---|---|---|---|
| Example 6 | 0.1 | — | — | — | — |
| Example 18 | — | 0.1 | — | — | — |
| Example 23 | — | — | 0.1 | — | — |
| Example 30 | — | — | — | 0.1 | — |
| Cetanol | 2.0 | 2.0 | 2.0 | 2.0 | 2.0 |
| PEG-20 | 1.0 | 1.0 | 1.0 | 1.0 | 1.0 |
| Sorbitan Monostearate | 1.0 | 1.0 | 1.0 | 1.0 | 1.0 |
| Mineral oil | 10.0 | 10.0 | 10.0 | 10.0 | 10.0 |
| Trioctanoate | 5.0 | 5.0 | 5.0 | 5.0 | 5.0 |
| Triethaonlamine | 0.5 | 0.5 | 0.5 | 0.5 | 0.5 |
| Carbomer | 0.2 | 0.2 | 0.2 | 0.2 | 0.2 |
| Glycerin | 5.0 | 5.0 | 5.0 | 5.0 | 5.0 |
| Propylene glycol | 3.0 | 3.0 | 3.0 | 3.0 | 3.0 |
| Antiseptic | trace amount | trace amount | trace amount | trace amount | trace amount |
| Flavor | trace amount | trace amount | trace amount | trace amount | trace amount |
| Distilled water | to 100 | to 100 | to 100 | to 100 | to 100 |

Preparation Example 4

Preparation of Ointment

The preparations were manufactured as described in following Table 5.

TABLE 5

| Composition (% of weight) | Preparation 4 a | b | c | d | Comparative preparation 4 |
|---|---|---|---|---|---|
| Example 6 | 0.1 | — | — | — | — |
| Example 18 | — | 0.1 | — | — | — |
| Example 23 | — | — | 0.1 | — | — |
| Example 30 | — | — | — | 0.1 | — |
| diethyl sebacate | 8.0 | 8.0 | 8.0 | 8.0 | 8.0 |
| Spermaceti | 5.0 | 5.0 | 5.0 | 5.0 | 5.0 |
| Polyoxyethylene oleyl etherphosphate | 6.0 | 6.0 | 6.0 | 6.0 | 6.0 |
| Sodium benzoates | trace amount | trace amount | trace amount | trace amount | trace amount |
| Vaseline | to 100 | to 100 | to 100 | to 100 | to 100 |

Preparation Example 5

Preparation of Essence

The preparations were manufactured as described in following Table 6.

TABLE 6

| Composition (% of weight) | Preparation 5 a | b | c | d | Comparative preparation 5 |
|---|---|---|---|---|---|
| Example 6 | 0.5 | — | — | — | — |
| Example 18 | — | 0.5 | — | — | — |
| Example 23 | — | — | 0.5 | — | — |
| Example 30 | — | — | — | 0.5 | — |
| Propylene glycol | 10.0 | 10.0 | 10.0 | 10.0 | 10.0 |
| Glycerin | 10.0 | 10.0 | 10.0 | 10.0 | 10.0 |
| Sodium hyaluronate solution (1%) | 5.0 | 5.0 | 5.0 | 5.0 | 5.0 |
| Ethanol | 5.0 | 5.0 | 5.0 | 5.0 | 5.0 |
| Polyoxyethylene hydrogenated caster oil | 1.0 | 1.0 | 1.0 | 1.0 | 1.0 |
| Methyl parahydroxybenzoate | 0.1 | 0.1 | 0.1 | 0.1 | 0.1 |
| Carbomer | 0.4 | 0.4 | 0.4 | 0.4 | 0.4 |
| Flavor | trace amount | trace amount | trace amount | trace amount | trace amount |
| Distilled water | to 100 | to 100 | to 100 | to 100 | to 100 |

Preparation Example 6

Preparation of Pack

The preparations were manufactured as described in following Table 7.

TABLE 7

| Composition (% of weight) | Preparation 6 a | b | c | d | Comparative preparation 6 |
|---|---|---|---|---|---|
| Example 6 | 0.1 | — | — | — | — |
| Example 18 | — | 0.1 | — | — | — |
| Example 23 | — | — | 0.1 | — | — |
| Example 30 | — | — | — | 0.1 | — |
| Glycerin | 5.0 | 5.0 | 5.0 | 5.0 | 5.0 |
| Propylene glycol | 4.0 | 4.0 | 4.0 | 4.0 | 4.0 |
| Polyvinyl alcohol | 15.0 | 15.0 | 15.0 | 15.0 | 15.0 |
| Ethanol | 8.0 | 8.0 | 8.0 | 8.0 | 8.0 |
| Polyoxyethylene hydrogenated caster oil | 1.0 | 1.0 | 1.0 | 1.0 | 1.0 |
| Polyoxyethylene oleyl ether phosphate | 1.0 | 1.0 | 1.0 | 1.0 | 1.0 |
| Methyl parahydroxybenzoate | 0.2 | 0.2 | 0.2 | 0.2 | 0.2 |
| Flavor | trace amount | trace amount | trace amount | trace amount | trace amount |
| Distilled water | to 100 | to 100 | to 100 | to 100 | to 100 |

Clinical Experimental 1

Inhibitory Effect on Pigmentation

To test the inhibiting activity of the Preparations 1 to 6 and Comparative Preparations 1 to 6 manufactured from the above-described Preparation Examples, the experiment was performed as follows.

After selecting the healthy 80 volunteers, aluminum foil with the diameter of 6 mm which has 7 holes in 2 lines, respectively, was attached to the humeral regions of both arms of volunteers, and 60 mJ/cm$^2$ of radiation was exposed to the region positioning at 10 cm away from the arms using by ORIEL solar simulator 1000 W. The humeral regions were washed with 70% ethanol before exposure. The applications of the Preparations 1 to 6 and Comparative Preparations 1 to 6 had been applied to the same line of the aluminum foil from 3 days before the exposure to 8 days after the exposure. The Preparation 6 and Comparative Preparation 6 were detached 15 mins after the application.

The test was performed in 4 test groups consisting of 20 people, respectively. The inhibitory effect on pigmentation was examined by naked eye by comparing Preparations with Comparative Preparations and the result of inhibitory activities were classified into three groups, i.e., more potent activity (++), potent activity(+), and no activity(−).

Table 8 shows the clinical result after the application of Preparations and Comparative Preparations.

TABLE 8

| Test samples | | ++ (persons) | + (persons) | − (persons) |
|---|---|---|---|---|
| Comparative Preparation 1 | | 0 | 2 | 18 |
| Preparation 1 | a | 3 | 8 | 9 |
| | b | 5 | 9 | 6 |
| | c | 3 | 7 | 20 |
| | d | 4 | 8 | 8 |
| Comparative Preparation 2 | | 0 | 3 | 17 |
| Preparation 2 | a | 5 | 9 | 6 |
| | b | 4 | 8 | 8 |
| | c | 6 | 9 | 5 |
| | d | 3 | 10 | 7 |
| Comparative Preparation 3 | | 0 | 3 | 17 |
| Preparation 3 | a | 5 | 10 | 5 |
| | b | 9 | 4 | 7 |
| | c | 6 | 9 | 5 |
| | d | 4 | 7 | 9 |
| Comparative Preparation 4 | | 0 | 3 | 17 |
| Preparation 4 | a | 5 | 8 | 7 |
| | b | 3 | 9 | 8 |
| | c | 4 | 8 | 8 |
| | d | 2 | 9 | 9 |
| Comparative Preparation 5 | | 0 | 3 | 17 |
| Preparation 5 | a | 3 | 7 | 10 |
| | b | 5 | 6 | 9 |
| | c | 4 | 10 | 6 |
| | d | 2 | 11 | 7 |
| Comparative Preparation 6 | | 0 | 4 | 16 |
| Preparation 6 | a | 8 | 5 | 7 |
| | b | 6 | 6 | 8 |
| | c | 5 | 9 | 6 |
| | d | 4 | 9 | 7 |

As shown in Table 8, it had been confirmed that the Preparations 1 to 6 containing the compounds of the present invention showed potent skin-whitening activity compared with Comparative Preparations.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, novel derivatives of cyclic compound have potent inhibiting effect on melanin formation and skin hyper-pigmentation activity with no adverse response to skin, therefore, they can be used as the therapeutics for treating and preventing the skin disease caused by over-reproduced melanin.

The invention claimed is:

1. A pharmaceutical composition comprising an efficient amount of a cyclic compound selected from the group consisting of:
   1-2-bis-octyloxy-cyclohexane,
   butyric acid 2-butyryloxy-trans-cyclohexyl ester,
   pentanoic acid 2-pentanoyloxy-trans-cyclohexyl ester,
   hexanoic acid 2-hexanoyloxy-trans-cyclohexyl ester,
   heptanoic acid 2-heptanoyloxy-trans-cyclohexyl ester,
   octanoic acid 2-octanoyloxy-trans-cyclohexyl ester,
   2-ethyl-hexanoic acid 2-(2-ethyl-hexanoyloxy)-trans-cyclohexyl ester,
   nonanoic acid 2-nonanoyloxy-trans-cyclohexyl ester,
   decanoic acid 2-decanoyloxy-trans-cyclohexyl ester,
   lauric acid 2-lauroyloxy-trans-cyclohexyl ester
   octanoic acid 2-octanoyloxy-trans-cyclopentyl ester,
   2-ethyl-hexanoic acid 2-(2-ethyl-hexanoyloxy)-trans-cyclopentyl ester,
   octanoic acid 2-octanoyloxy-phenyl ester,
   octanoic acid 3-octanoyloxy-naphthalene-2-yl ester,
   2-ethyl-hexanoic acid 3-(2-ethyl-hexanoyloxy)-naphthalene-2-yl ester,
   octanoic acid 3-octanoyloxy-pyridine-2-yl ester,
   octanoic acid 2,3-bis-octanoyloxy-cyclohexyl ester,
   myo-inositol hexa-O-butanoate,
   arabinopyranose 1,2,3,4-tetra-O-(3-methyl-2-butenoate),
   methyl-α-D-glucose tetra-O-butanoate,
   1,2-bis-(3-methyl-butoxy)-cyclohexane,
   1,2-bis-pentyloxy-cyclohexane, and
   1,2-bis-hexyloxy-cyclohexane,
or a pharmaceutically acceptable salt thereof as an active ingredient in an amount effective to treat the skin disease caused by over-reproduced melanin, together with pharmaceutically acceptable carriers or diluents, wherein the pharmaceutical composition is a topical preparation selected from cream, gel, patch, spray, ointment, lotion, liniment, and cataplasma.

2. The pharmaceutical composition according to claim 1, wherein said the skin disease is selected from skin discoloration, freckles, or skin darkening after skin inflammation and purpura senile caused by over-reproduced melanin.

3. A method for inhibiting over-production of melanin, comprising the step of administering a therapeutically effective amount of the pharmaceutical composition of claim 1 into the mammals including human suffering from said disease caused by over-production of melanin.

4. A cosmetic composition comprising an efficient amount of a cyclic compound selected from the group consisting of:
   1-2-bis-octyloxy-cyclohexane,
   butyric acid 2-butyryloxy-trans-cyclohexyl ester,
   pentanoic acid 2-pentanoyloxy-trans-cyclohexyl ester,
   hexanoic acid 2-hexanoyloxy-trans-cyclohexyl ester,
   heptanoic acid 2-heptanoyloxy-trans-cyclohexyl ester,
   octanoic acid 2-octanoyloxy-trans-cyclohexyl ester,
   2-ethyl-hexanoic acid 2-(2-ethyl-hexanoyloxy)-trans-cyclohexyl ester,
   nonanoic acid 2-nonanoyloxy-trans-cyclohexyl ester,
   decanoic acid 2-decanoyloxy-trans-cyclohexyl ester,
   lauric acid 2-lauroyloxy-trans-cyclohexyl ester
   octanoic acid 2-octanoyloxy-trans-cyclopentyl ester,
   2-ethyl-hexanoic acid 2-(2-ethyl-hexanoyloxy)-trans-cyclopentyl ester,
   octanoic acid 2-octanoyloxy-phenyl ester,
   octanoic acid 3-octanoyloxy-naphthalene-2-yl ester,
   2-ethyl-hexanoic acid 3-(2-ethyl-hexanoyloxy)-naphthalene-2-yl ester,
   octanoic acid 3-octanoyloxy-pyridine-2-yl ester,
   octanoic acid 2,3-bis-octanoyloxy-cyclohexyl ester,
   myo-inositol hexa-O-butanoate,
   arabinopyranose I,2,3,4-tetra-O-(3-methyl-2-butenoate),
   methyl-α-D-glucose tetra-O-butanoate,
   1,2-bis-(3-methyl-butoxy)-cyclohexane,
   1,2-bis-pentyloxy-cyclohexane, and 1,2-bis-hexyloxy-cyclohexane, or a pharmacologically acceptable salt thereof as an active ingredient in an effective amount to treat and prevent the skin disease caused by over-reproduced melanin and a pharmaceutically acceptable carrier, wherein said cosmetic composition is selected from skin lotion, skin softener, skin toner, astringent, lotion, milk lotion, moisture lotion, nutrient lotion, massage cream, nutrient cream, moisture cream, hand cream, foundation, essence, nutrient essence, pack, cleansing foam, cleansing lotion, cleansing cream, body lotion, body cleanser, treatment, and beauty solution.

5. The cosmetic composition according to claim 4, wherein said cosmetic composition comprises 0.001 to 40 w/w % of the compound.

6. The pharmaceutical composition according to claim 1, wherein the cyclic compound is 2-ethyl-hexanoic acid 2-(2-ethyl-hexanoyloxy)-trans-cyclohexyl ester or 2-ethyl-hexanoic acid 2-(2-ethyl-hexanoyloxy)-trans-cyclopentyl ester.

7. The cosmetic composition according to claim 4, wherein the cyclic compound is 2-ethyl-hexanoic acid 2-(2-ethyl-hexanoyloxy)-trans-cyclohexyl ester or 2-ethyl-hexanoic acid 2-(2-ethyl-hexanoyloxy)-trans-cyclopentyl ester.

* * * * *